United States Patent [19]
Luengo et al.

[11] Patent Number: 6,096,897
[45] Date of Patent: Aug. 1, 2000

[54] ENDOTHELIN RECEPTOR ANTAGONISTS

[75] Inventors: Juan Ignacio Luengo, Audubon; John Duncan Elliott, Wayne, both of Pa.

[73] Assignee: SmithKline Beecham Corporation, Philadelphia, Pa.

[21] Appl. No.: 09/342,989

[22] Filed: Jun. 29, 1999

Related U.S. Application Data

[62] Division of application No. 09/227,361, Jan. 8, 1999, which is a division of application No. 09/121,545, Jul. 23, 1998, which is a continuation of application No. 08/718,562, filed as application No. PCT/US96/12581, Aug. 2, 1996, abandoned.

[60] Provisional application No. 60/001,792, Aug. 2, 1995, and provisional application No. 60/010,982, Feb. 1, 1996.

[51] Int. Cl.$^7$ .................. A61K 31/41; C07D 405/02
[52] U.S. Cl. ............................. 548/256; 514/359
[58] Field of Search ................. 548/256; 514/359

[56] References Cited

U.S. PATENT DOCUMENTS 3,703,513  11/1972  Yamamoto et al. .
4,965,282  10/1990  Takamura et al. .

FOREIGN PATENT DOCUMENTS 0 714 897 A1  6/1996  European Pat. Off. .
WO94/22830  10/1994  WIPO .

*Primary Examiner*—Robert W. Ramsuer
*Attorney, Agent, or Firm*—Linda E. Hall; Stephen A. Venetianer; Charles M. Kinzig

[57] ABSTRACT

Novel pyrroles, pyrazoles and triazoles, pharmaceutical compositions containing these compounds and their use as endothelin receptor antagonists are described.

15 Claims, No Drawings

ENDOTHELIN RECEPTOR ANTAGONISTS

This is a divisional of prior application Ser. No. 09/227,361, filed Jan. 8, 1999; which is a divisional of prior application Ser. No. 09/121,545, filed Jul. 23, 1998; which is a continuation of prior application Ser. No. 08/718,562, filed Feb. 2, 1998 now abandoned; which is a 371 of International Application No. PCT/US96/12581, filed Aug. 2, 1996; which claims the benefit of priority from the following provisional applications 60/001,792, filed Aug. 2, 1995 and 60/010,982, filed Feb. 1, 1996.

FIELD OF INVENTION

The present invention relates to novel pyrroles, pyrazoles and triazoles, pharmaceutical compositions containing these compounds and their use as endothelin receptor antagonists.

Endothelin (ET) is a highly potent vasoconstrictor peptide synthesized and released by the vascular endothelium. Endothelin exists as three isoforms. ET-1, ET-2 and ET-3. [Unless otherwise stated "endothelin" shall mean any or all of the isoforms of endothelin]. Endothelin has profound effects on the cardiovascular system, and in particular, the coronary, renal and cerebral circulation. Elevated or abnormal release of endothelin is associated with smooth muscle contraction which is involved in the pathogenesis of cardiovascular, cerebrovascular, respiratory and renal pathophysiology. Elevated levels of endothelin have been reported in plasma from patients with essential hypertension, acute myocardial infarction, subarachnoid hemorrhage, atherosclerosis, and patients with uraemia undergoing dialysis.

In vivo, endothelin has pronounced effects on blood pressure and cardiac output. An intravenous bolus injection of ET (0.1 to 3 nmol/kg) in rats causes a transient, dose-related depressor response (lasting 0.5 to 2 minutes) followed by a sustained, dose-dependent rise in arterial blood pressure which can remain elevated for 2 to 3 hours following dosing. Doses above 3 nmol/kg in a rat often prove fatal.

Endothelin appears to produce a preferential effect in the renal vascular bed. It produces a marked, long-lasting decrease in renal blood flow, accompanied by a significant decrease in GFR, urine volume, urinary sodium and potassium excretion. Endothelin produces a sustained antinatriuretic effect, despite significant elevations in atrial natriuretic peptide. Endothelin also stimulates plasma renin activity. These findings suggest that ET is involved in the regulation of renal function and is involved in a variety of renal disorders including acute renal failure, cyclosporine nephrotoxicity, radio contrast induced renal failure and chronic renal failure.

Studies have shown that in vivo, the cerebral vasculature is highly sensitive to both the vasodilator and vasoconstrictor effects on endothelin. Therefore, ET may be an important mediator of cerebral vasospasm, a frequent and often fatal consequence of subarachnoid hemorrhage.

ET also exhibits direct central nervous system effects such as severe apnea and ischemic lesions which suggests that ET may contribute to the development of cerebral infarcts and neuronal death.

ET has also been implicated in myocardial ischemia (Nichols et al., Br. J. Pharm. 99: 597–601, 1989 and Clozel and Clozel, Circ. Res., 65: 1193–1200, 1989) coronary vasospasm (Fukuda et al., Eur. J. Pharm. 165: 301–304, 1989 and Lüscher, Circ. 83: 701, 1991) heart failure, proliferation of vascular smooth muscle cells, (Takagi, Biochem & Biophys. Res. Commun.; 168: 537–543, 1990, Bobek et al., Am. J. Physiol. 258:408–C415, 1990) and atherosclerosis, (Nakaki et al., Biochem. & Biophys. Res. Commun. 158: 880–881, 1989, and Lerman et al., New Eng. J. of Med. 325: 997–1001, 1991). Increased levels of endothelin have been shown after coronary balloon angioplastry (Kadel et al., No. 2491 Circ. 82: 627, 1990).

Further, endothelin has been found to be a potent constrictor of isolated mammalian airway tissue including human bronchus (Uchida et al., Eur J. of Pharm. 154: 227–228 1988, LaGente, Clin. Exp. Allergy 20: 343–348, 1990; and Springall et al., Lancet, 337: 697–701, 1991). Endothelin may play a role in the pathogenesis of interstitial pulmonary fibrosis and associated pulmonary hypertension, Glard et al., Third International Conference on Endothelin, 1993, p. 34 and ARDS (Adult Respiratory Distress Syndrome), Sanai et al., Supra. p. 112.

Endothelin has been associated with the induction of hemorrhagic and necrotic damage in the gastric mucosa (Whittle et al., Br. J. Pharm. 95: 1011–1013, 1988); Raynaud's phenomenon, Cinniniello et al., Lancet 337: 114–115, 1991); Crohn's Disease and ulcerative colitis, Munch et al., Lancet, Vol. 339, p. 381; Migraine (Edmeads, Headache, February 1991 p 127); Sepsis (Weitzberg et al., Circ. Shock 33: 222–227, 1991; Pittet et al., Ann. Surg. 213: 262–264, 1991), Cyclosporin-induced renal failure or hypertension (Eur. J. Pharmacol., 180: 191–192, 1990, Kidney Int. 37: 1487–1491, 1990) and endotoxin shock and other endotoxin induced diseases (Biochem. Biophys. Res. Commun., 161: 1220–1227, 1989, Acta Physiol. Scand. 137: 317–318, 1989) and inflammatory skin diseases. (Clin Res. 41:451 and 484, 1993).

endothelin has also been implicated in preclampsia of pregnancy. Clark et al., Am. J. Obstet. Gynecol. March 1992, p. 962–968; Kamor et al., N. Eng. J. of Med., Nov. 22, 1990, p. 1486–1487; Dekker et al., Eur J. Ob. and Gyn. and Rep. Bio. 40(1991) 215–220; Schiff et al., Am. J. Ostet. Gynecol. February 1992, p. 624–628; diabetes mellitus. Takahashi et al., Diabetologia (1990) 33:306–310; and acute vascular rejection following kidney transplant, Watschinger et al., Transplantation Vol. 52, No. 4, pp. 743–746.

Endothelin stimulates both bone resportion and anabolism and may have a role in the coupling of bone remodeling. Tatrai et al., Endocrinology, Vol. 131, p. 603–607.

Endothelin has been reported to stimulate the transport of sperm in the uterine cavity, Casey et al., J. Clin. Endo and Metabolism, Vol. 74, Vol. 1, p. 223–225, therefore endothelin antagonists may be useful as male contraceptives. Endothelin modulates the ovarian/menstrual cycle, Kenegsberg, J. of Clin. Endo. and Met., Vol. 74, No. 1, p. 12, and may also play a role in the regulation of penile vascular tone in man. Lau et al., Asia Pacific J. of Pharm., 1991, 6:287–292 and Tejada et al., J. Amer. Physio. Soc. 1991, H1078–H1085. Endothelin also mediates a potent contraction of human prostatic smooth muscle, Langenstroer et al., J. Urology, Vol. 149, p. 495–499.

Thus, endothelin receptor antagonists would offer a unique approach toward the pharmacotherapy of hypertension, acute and chronic renal failure, ischemia induced renal failure, sepsis-endotoxin induced renal failure, prophylaxis and/or treatment of radio-contrast induced renal failure, acute and chronic cyclosporin induced renal failure, cerebrovascular disease, cerebrovascular spasm, subarachnoid hemorrhage, myocardial ischemia, angina, congestive heart failure, acute coronary syndrome, myocardial salvage, unstable angina, asthma, primary pulmonary hypertension, pulmonary hypertension secondary to intrinsic pulmonary disease, atherosclerosis. Raynaud's phenomenon, ulcers, sepsis, migraine, glaucoma, endotoxin shock, endotoxin induced multiple organ failure or disseminated intravascular coagulation, cyclosporin-induced renal failure and as an adjunct in angioplasty for prevention of restenosis, diabetes, diabetic retinopathy, retinopathy, diabetic nepthropathy, diabetic macrovascular disease, atherosclerosis, preclampsia of pregnancy, bone remodeling, kidney transplant, male contraceptives, infertility and priaprism and benign prostatic hypertrophy.

SUMMARY OF THE INVENTION

This invention comprises compounds represented by Formula (I) and pharmaceutical compositions containing these compounds, and their use as endothelin receptor antagonists which are useful in the prevention or treatment of a variety of cardiovascular and renal diseases including but not limited to: hypertension, acute and chronic renal failure, cyclosporine induced nepthrotoxicity, benign prostatic hypertrophy, pulmonary hypertension, migraine, stroke, subarachnoid hemorrhage, cerebrovascular vasospasm, myocardial ischemia, angina, congestive heart failure, unstable angina, coronary vasospasm and myocardial salvage, the sequelae of diabetes including but not limited to: atherosclerosis, diabetic nephropathy, diabetic retinopathy, retinopathy, diabetic macrovascular disease; and as an adjunct in angioplasty for prevention of restenosis.

This invention further constitutes a method for antagonizing endothelin receptors in an animal, including humans, which comprises administering to an animal in need thereof an effective amount of a compound of Formula (I).

This invention also constitutes intermediates represented by Formula (II). In a further aspect, the present invention provides a process for the preparation of a compound of Formula (I)(d).

DETAILED DESCRIPTION OF THE INVENTION

The compounds of this invention are represented by structural Formula (I):

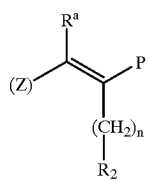

(I)

wherein (Z) is

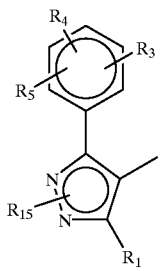

(d)

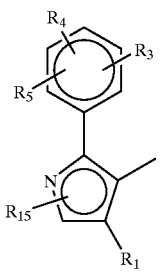

(e)

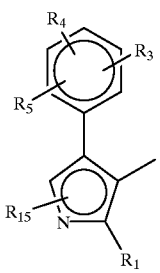

(f)

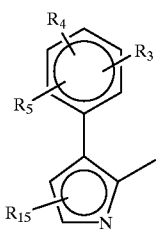

(g)

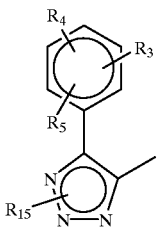

(h)

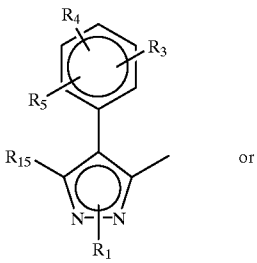

(i)

or

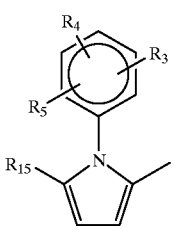

(j)

P is tetrazol-5-yl, $CO_2R_6$ or $C(O)N(R_6)S(O)_qR_{10}$;
$R^a$ is independently hydrogen or $C_{1-6}$alkyl;

$R_1$ is independently hydrogen, Ar, $C_{1-6}$alkyl or $C_{1-6}$alkoxy;

$R_2$ is

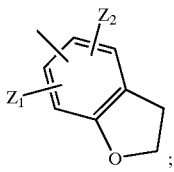
;

$R_3$ and $R_5$ are independently $R_{13}$OH, $C_{1-8}$alkoxy, $S(O)_q R_{11}$, $N(R_6)_2$, $NO_2$, Br, F, I, Cl, $CF_3$, $NHCOR_6$, $R_{13}CO_2R_7$, —X—$R_9$—Y, —X$C(R_6)_2OR_6$, —$(CH_2)_m X'R_8$ or —X$(CH_2)_nR_8$ wherein each methylene group within —X$(CH_2)_nR_8$ may be unsubstituted or substituted by one or two —$(CH_2)_n$Ar groups;

$R_4$ is independently $R_{11}$, OH, $C_{1-5}$alkoxy, $S(O)_qR_{11}$, $N(R_6)_2$, Br, F, I, Cl or $NHCOR_6$, wherein the $C_{1-5}$alkoxy may be unsubstituted or substituted by OH, methoxy or halogen;

$R_6$ is independently hydrogen or $C_{1-8}$alkyl;

$R_7$ is independently hydrogen, $C_{1-10}$alkyl, $C_{2-10}$alkenyl or $C_{2-8}$alkynyl, all of which may be unsubstituted or substituted by one or more OH, $N(R_6)_2$, $CO_2R_{12}$, halogen or $XC_{1-10}$alkyl; or $R_7$ is $(CH_2)_n$Ar;

$R_8$ is independently $R_{11}$, $CO_2R_7$, $CO_2C(R_{11})_2O(CO)XR_7$, $PO_3(R_7)_2$, $SO_2NR_7R_{11}$, $NR_7SO_2R_{11}$, $CONR_7SO_2R_{11}$, $SO_3R_7$, $SO_2R_7$, $P(O)(OR_7)R_7$, CN, $CO_2(CH_2)_mC(O)N(R_6)_2$, $C(R_{11})_2N(R_7)_2$, $C(O)N(R_6)_2$, $NR_7C(O)NR_7SO_2R_{11}$, $OR_6$, or tetrazole which is substituted or unsubstituted by $C_{1-6}$alkyl;

$R_9$ is independently a bond, $C_{1-10}$alkylene, $C_{1-10}$alkenylene, $C_{1-10}$alkylidene, $C_{1-10}$alkynylene, all of which may be linear or branched, or phenylene, all of which may be unsubstituted or substituted by one or more OH, $N(R_6)_2$, COOH or halogen;

$R_{10}$ is independently $C_{1-10}$alkyl, $N(R_6)_2$ or Ar;

$R_{11}$ is independently hydrogen, Ar, $C_{1-8}$alkyl, $C_{2-8}$alkenyl, $C_{2-8}$alkynyl, all of which may be substituted or unsubstituted by one or more HO, $CH_2OH$, $N(R_6)_2$, or halogen;

$R_{12}$ is independently hydrogen, $C_{1-6}$alkyl, $C_{2-6}$alkenyl or $C_{2-7}$alkynyl;

$R_{13}$ is independently divalent Ar, $C_{1-10}$alkylene, $C_{1-10}$alkylidene, $C_{2-10}$alkenylene, all of which may be unsubstituted or substituted by one or more OH, $CH_2OH$, $N(R_6)_2$ or halogen;

$R_{14}$ is independently hydrogen, $C_{1-10}$alkyl, $XC_{1-10}$alkyl, Ar or XAr;

$R_{15}$ is independently hydrogen, Ar, $C_{1-6}$alkyl, or XAr;

$R_{16}$ is independently $C_{1-6}$alkyl or phenyl substituted by one or more $C_{1-6}$alkyl, OH, $C_{1-5}$alkoxy, $S(O)_qR_6$, $N(R_6)_2$, Br, F, I, Cl, $CF_3$ or $HNCOR_6$;

X is independently $(CH_2)_n$, O, $NR_6$ or $S(O)_q$;

X' is independently O, $NR_6$ or $S(O)_q$;

Y is independently $CH_3$ or $X(CH_2)_n$Ar;

Ar is:

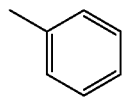
(a)

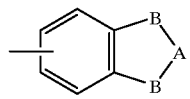
(b)

naphthyl, indolyl, pyridyl, thienyl, oxazolidinyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $Z_1$ or $Z_2$ groups;

A is independently C=O, or $(C(R_6)_2)_m$;

B is independently —$CH_2$— or —O—;

$Z_1$ and $Z_2$ are independently hydrogen, $XR_6$, $C_{1-8}$alkyl, $(CH_2)_qCO_2R_6$, $C(O)N(R_6)_2$, CN, $(CH_2)_nOH$, $NO_2$, F, Cl, Br, I, $N(R_6)_2$, $NHC(O)R_6$, $O(CH_2)_mC(O)NR_aSO_2R_{16}$, $(CH_2)_mOC(O)NR_aSO_2R_{16}$, $O(CH_2)_m NR_aC(O)NR_aSO_2R_{16}$ tetrazolyl which may be substituted or unsubstituted by $C_{1-6}$alkyl, $CF_3$ or $C(O)R_6$;

m is independently 1 to 3;

n is independently 0 to 6;

q is independently 0, 1 or 2;

provided $R_3$, $R_4$ and $R_5$ are not O—O$(CH_2)_n$Ar or O—$OR_6$;

or a pharmaceutically acceptable salt thereof.

All alkyl, alkenyl, alkynyl and alkoxy groups may be straight or branched.

Halogen may be Br, Cl, F or I.

The compounds of the present invention may contain one or more asymmetric carbon atoms and may exist in racemic and optically active form. All of these compounds and their diastereoisomers are contemplated to be within the scope of the present invention.

Preferred compounds are those wherein:

P is $CO_2R_6$; more preferably P is $CO_2H$.

$R_1$ is hydrogen.

$Z_1$ and $Z_2$ are independently hydrogen, $CO_2R_6$, $(CH_2)_nOH$, $C_{1-4}$alkyl or $C_{1-6}$ alkoxy, e.g. methoxy.

$R_3$ and $R_5$ are independently hydrogen, $CO_2R_6$, OH, $C_{1-8}$alkoxy, $C_{1-8}$alkyl, $N(R_6)_2$, $NO_2$, Br, F, Cl, I, $R_{13}CO_2R_7$, $X(CH_2)_nR_8$, $(CH_2)_mX'R_8$, or $X(C(R_6)_2)_mOR_6$.

In the context of the group $R_3$ and $R_5$ preferably do not represent hydrogen. In particular in the group $R_3$ preferably represents Br, Cl, $C_{1-8}$alkoxy e.g. methoxy; $X(CH_2)_nR_8$, wherein X preferably represents O, n is 0, 1, or 2, and $R_8$ is preferably selected from:

$CO_2R_6$ wherein $R_6$ is preferably hydrogen;

$OR_6$ wherein $R_6$ is preferably H;

tetrazolyl optionally substituted by $C_{1-8}$alkyl e.g. ethyl;

$CONR_7SO_2R_{11}$ wherein $R_7$ is H or $C_{1-8}$alkyl e.g. methyl, $R_{11}$ preferably is $C_{1-8}$alkyl (e.g. methyl, isopropyl, or t-butyl) or phenyl optionally substituted by Br, Cl, F, $C_{1-8}$alkyl e.g. methyl;

or $R_8$ is phenyl or pyridyl substituted by one or more Br, Cl, $CO_2H$, $CH_2OH$; and $R_5$ is $C_{1-8}$alkoxy e.g. methoxy, or $N(R_6)_2$ wherein $R_6$ preferably is H or methyl.

$R_4$ is hydrogen, OH, $C_{1-5}$alkoxy, $N(R_6)_2$, Br, F, Cl, I, $NHCOCH_3$, or $S(O)_q$ $C_{1-5}$alkyl wherein the $C_{1-5}$alkyl may be unsubstituted or substituted by OH, methoxy or halogen. $R_4$ is more preferably hydrogen.

$R_6$ is hydrogen or $C_{1-8}$alkyl e.g. methyl and ethyl.

$R_7$ is hydrogen, $C_{1-10}$alkyl, $C_{2-10}$alkenyl or $C_{2-8}$alkynyl, all of which may be unsubstituted or substituted by one or more OH, $N(R_6)_2$, $CO_2R_{12}$, halogen, or $R_7$ is $(CH_2)_n$Ar. When $R_7$ is $(CH_2)_n$Ar, n is preferably zero or 1 and Ar is preferably phenyl substituted or unsubstituted by halogen or $C_{1-5}$ alkoxy.

$R_{11}$ is hydrogen, phenyl, pyridyl wherein the phenyl and pyridyl may be substituted or unsubstituted by one or two $C_{1-4}$alkyl groups; $C_{1-8}$alkyl, $C_{2-8}$alkenyl, $C_{2-8}$alkynyl, all of which may be substituted or unsubstituted by one or more OH, $CH_2OH$, $N(R_6)_2$, or halogen;

$R_{12}$ is hydrogen or $C_{1-6}$alkyl.

$R_{13}$ is phenyl, pyridyl, or $C_{2-10}$alkylene, all of which may be unsubstituted or substituted by one or more $CO_2R_6$, OH, $CH_2OH$, $N(R_6)_2$, or halogen;

$R_{15}$ is preferably hydrogen or $C_{1-6}$alkyl e.g. ethyl, isopropyl, n-butyl, cyclopropylmethyl or cyclopropylethyl.

(Z) is preferably (d).

Preferred compounds are:

(E)-3-[1-n-Butyl-5-[2-(2-carboxy-6-chlorophenyl)methyoxy-4-chlorophenyl]-1H-pyrazol-4-yl]-2-[(5-methoxy-2,3-dihydrobenzofuran-6-yl)methyl]-prop-2-enoic acid;

(E)-3-[1-n-Butyl-5-[2-(2-carboxyphenyl)methoxy-4-chlorophenyl]-1H-pyrazol-4-yl]-2-[(5-methoxy-2,3-dihydrobenzofuran-6-yl)methyl]-prop-2-enoic acid;

(E)-3-[1-n-Butyl-5-[2-(2-carboxyphenyl)methoxy-4-methoxyphenyl]-1H-pyrazol-4-yl]-2-[(5-methoxy-2,3-dihydrobenzofuran-6-yl)methyl]-prop-2-enoic acid;

(E)-3-[1-n-Butyl-5-[2-(2-carboxy-6-chlorophenyl)methoxy-4-methoxyphenyl]-1H-pyrazol-4-yl]-2-[(5-methoxy-2,3-dihydrobenzofuran-6-yl)methyl]-prop-2-enoic acid;

(E)-3-[1-n-Butyl-5-[2-(2-carboxy-5-chlorophenyl)methoxy-4-methoxyphenyl]-1H-pyrazol-4-yl]-2-[(5-methoxy-2,3-dihydrobenzofuran-6-yl)methyl]-prop-2-enoic acid;

(E)-3-[1-n-Butyl-5-[2-(3-carboxy-2-pyridyl)methoxy-4-methoxyphenyl]-1H-pyrazol-4-yl]-2-[(5-methoxy-2,3-dihydrobenzofuran-5-yl)methyl]-prop-2-enoic acid; or (E)-3-[1-n-Butyl-5-[2-(2-carboxy-5-chlorophenyl)methoxy-4-chlorophenyl]-1H-pyrazol-4-yl]-2-[(5-methoxy-2,3-dihydrobenzofuran-6-yl)methyl]-prop-2-enoic acid.

The present invention provides compounds of Formula (I), which may be made by methods similar to those given below.

Compounds of the Formula (Id):

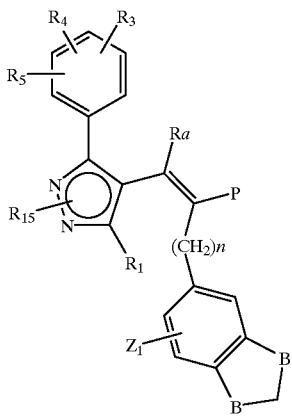

wherein one B is $CH_2$ and the other is O can be prepared by alkylating a ketone of Formula (2):

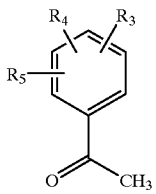

in dimethyl carbonate in the presence of sodium hydride to provide a b-keto ester of Formula (3).

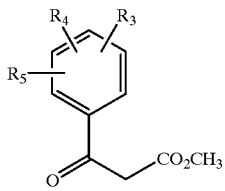

Condensation of a b-keto ester of Formula (3) with dimethyl formate dimethyl acetal in a suitable solvent such as toluene at approximately 95° C. affords a compound of Formula (4).

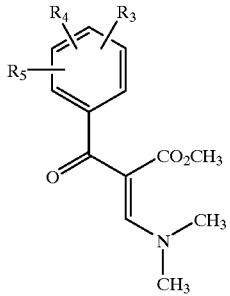

Treatment of a compound of Formula (4) with a hydrazine derivative of the Formula (5)

$R_{15}-NH-NH_2$  (5)

wherein $R_{15}$ is $C_{1-6}$ alkyl;

in suitable solvents such as methanol and water in the presence of sodium acetate provides a pyrazole of Formula (6).

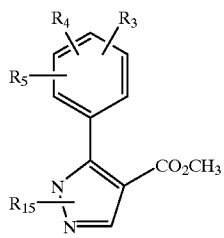

(6)

Reduction of an ester of Formula (6) with a reducing agent such as diisobutylalluminum hydride in a solvent such as dichloromethane followed by oxidation with an oxidant such as Jones reagent in acetone affords an aldehyde of Formula (7).

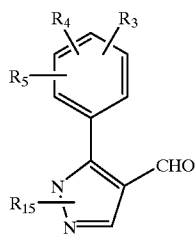

(7)

Knoevenagel condensation of an aldehyde of Formula (7) with a half acid of Formula (8), wherein $R_{16}$ is $C_{1-8}$ alkyl

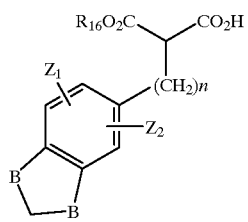

(8)

in a solvent such as benzene at reflux, in the presence of piperidinium acetate with azeotropic removal of water using a Dean-Stark apparatus to afford an ester of Formula (9).

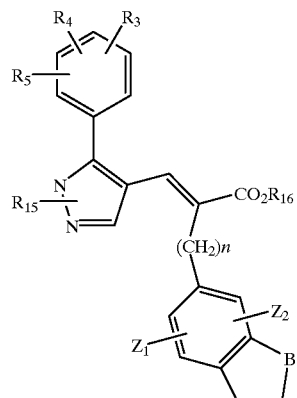

(9)

Followed if necessary and desired by:

1) deprotection and alkylation and hydrolysis of the $R_3$, $R_4$, $R_5$, $R_{15}$, $R_{16}$, $Z_1$ and $Z_2$ groups as required and;
2) salt formation Aldehyde condensation may be effected by heating in the presence of pyridine and acetic acid.

Conversion of an ester of formula (9) into an acid may be carried out using conventional deprotection techniques i.e. hydrolysis.

A half acid of Formula (8),

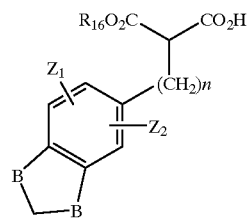

(8)

wherein $R_{16}$ is $C_{1-8}$ alkyl and n is 1, may be prepared starting from 4-methoxyphenol (10)

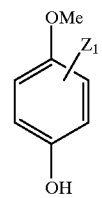

(10)

which upon bromination affords a bromobenzene of Formula (11).

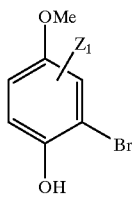

(11)

Alkylation of phenol of Formula (11) with 1,2-dichloroethane under phase transfer reaction conditions provides a compound of Formula (12).

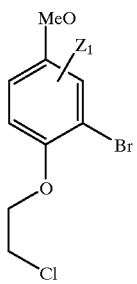

(12)

Treatment of bromobenzene of Formula (12) with an organolithium reagent such n-butyllithium or metal such as magnesium in a solvent such as tetrahydrofuran affords dihydrobenzofuran of Formula (13).

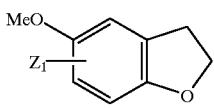

(13)

Bromination of a compound of Formula (13) with hexamethylenetetraamine hydrobromide perbromide in a solvent such as dichloromethane provides bromodihydrobenzofuran of Formula (14).

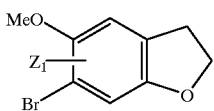

(14)

Metal-halogen exchange of compound of Formula (14) using an organolithium reagent such n-butyllithium in a solvent such as tetrahydrofuran affords an aldehyde of Formula (15).

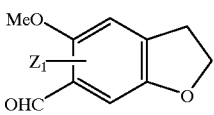

(15)

Condensation of an aldehyde of Formula (15) with dialkyl malonate such as diethyl malonate in the presence of piperidine and acetic acid in a solvent such as benzene provides an a,b-unsaturated ester of Formula (16).

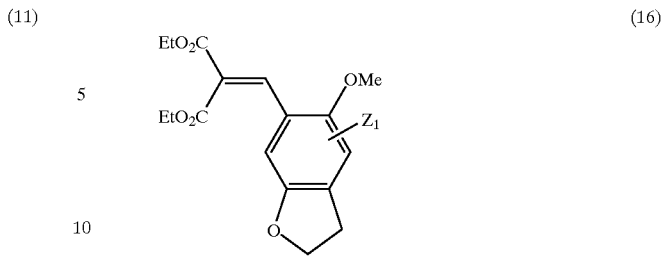

(16)

Treatment of an a,b-unsaturated ester of Formula (16) with sodium borohydride in ethanol followed by mono saponification with aqueous sodium hydroxide in a solvent such as ethanol affords, after acidification with aqueous hydrochloric acid, an acid of formula (8), whereas $R_{16}$ is ethyl and n is 1.

Other compounds of Formula (Id) may be made by methods well known in the art.

The invention also is a process for preparing compounds of Formula (Id) by:

(a) reaction of a compound of Formula (II)

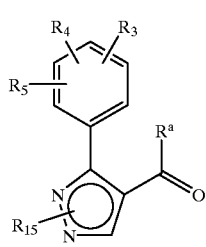

(II)

or a protected form or precursor thereof (as defined hereinafter) with a compound of Formula (8)

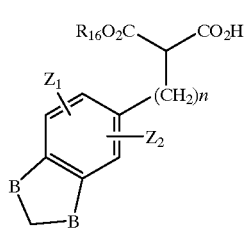

(8)

wherein one B is $CH_2$ and the other is O, and $Z_1$, $Z_2$ and $R_{16}$ are as defined for Formula (Id) hereinabove;

followed if necessary or desired by:

(b) conversion of one compound of Formula (Id) into a different compound of Formula (Id) e.g.
   (i) when Formula (Id) contains a group $CO_2R_6$, $CO_2R_7$ or $CO_2R_{12}$, or $CO_2R_{16}$ wherein $R_6$, $R_7$, $R_{12}$ or $R_{16}$ is alkyl, conversion to a corresponding compound where $R_6$, $R_7$, $R_{12}$ or $R_{16}$ represents hydrogen;
   (ii) when Formula (Id) contains hydroxy group (e.g. in $R_3$, $R_4$ or $R_5$) conversion to a different group, e.g. group $(CH_2)Ar$ where Ar is optionally substituted phenyl, by method well known in the art; and/or (c) salt formation.

It will be appreciated by those skilled in the art that the substituents $R_{15}$, $R_3$, $R_4$ and $R_5$ and be introduced at any appropriate stage of the synthesis, preferably at an early stage, using methods well known in the art. In some of the reactions depicted above, particularly those in the early stages of the overall synthesis, one or more of the substituents $R_{15}$, $R_3$, $R_4$ and $R_5$ may therefore represent a precursor for the eventual substituent. A precursor for any of the substituents $R_{15}$, $R_3$, $R_4$ and $R_5$ means a group which may be derivatised or converted into the desired group $R_{15}$, $R_3$, $R_4$ and $R_5$. It will be further appreciated that it may be necessary or desirable to protect certain of these substituents (or their precursors) at various stages in the reaction sequence. Suitable precursors and protecting groups as well known to those skilled in the art, as the methods for their conversion of removal respectively.

In another aspect the invention provides for an intermediate of the formula (II) wherein $R_{15}$, $R_3$, $R_4$, $R_5$ and $R^a$ are as described for Formula (I) Compounds of Formula (Ii)

(Ii)

wherein one B is $CH_2$ and the other is O;
can be prepared starting by commercially available ketones of Formula (17)

(17)

by reaction with diethyl oxalate of Formula (18)

(18)

in the presence of a base such as sodium ethoxide in a solvent such as ethanol to produce a diketone of Formula (19).

(19)

Reaction of a diketone of Formula (19) with hydrazine derivative of Formula (20)

(20)

in a suitable solvent such as ethanol at reflux provides a pyrazole of Formula (21).

(21)

Sponification of an ester of Formula (21) using lithium hydroxide in a solvent such as aqueous methanol affords, after acidification an acid of the Formula (22), (22)

which can be subsequently converted to the corresponding N-methoxy-N-methylamide of Formula (23)

(23)
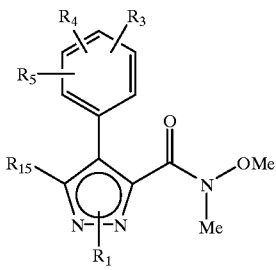

by treatment with methyl chloroformate followed by N,O-dimethylhydroxylamine hydrochloride in the presence of a base such as N-methylpiperidine. Compound of Formula (23) can be treated with an organometallic reagent $R^q$—M wherein $R^a$ is $C_{1-6}$ alkyl and M is Li or MgCl; to provide a compound of Formula (24), wherein $R^a$ is $C_{1-6}$alkyl.

(24)
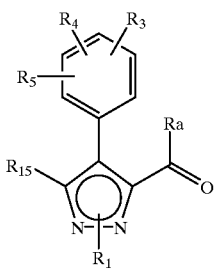

Alternatively, reaction of compound (24), wherein $R^a$ is $C_{1-6}$alkyl, with Lawesson's reagent in a suitable solvent such as tetrahydrofuran affords a thione of Formula (25),

(25)
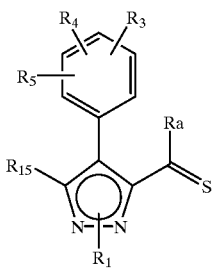

which can be treated with the diazoester (26)

(26)
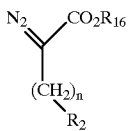

in refluxing tetrahydrofuran to provide a thiirane of Formula (27).

(27)
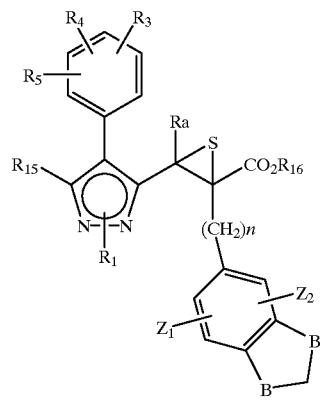

Treatment of a thiirane of Formula (27) with trimethylphosphite at reflux in a solvent such as chloroform provides compounds of Formula (28), wherein $R^a$ is $C_{1-6}$alkyl.

(28)
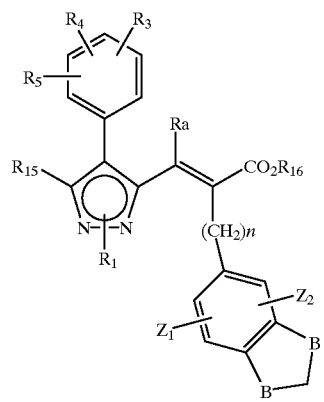

Saponification of an ester of Formula (28) using lithium hydroxide in a solvent such as aqueous methanol affords, after acidification with acetic acid, an acid of the Formula (Ii), wherein P is $CO_2H$.

Compounds of the Formula (Ie)

(Ie)
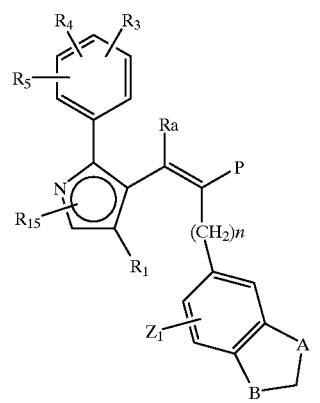

wherein one B is $CH_2$ and the other is O; can be prepared following the steps outlined in the following Scheme

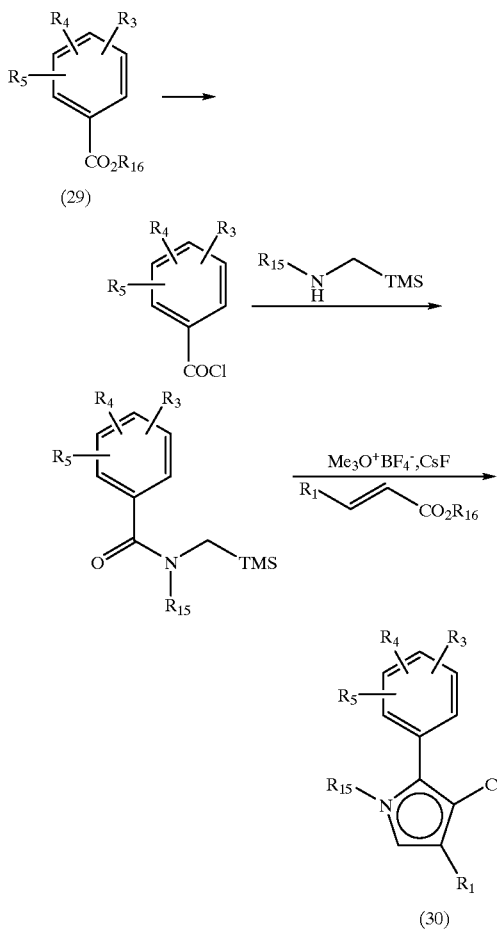

(29)

(30)

starting from an aryl ester of Formula (29), wherein $R_{16}$ is $R_{1-8}$ alkyl, to provide a pyrrole of Formula (30). Compound of Formula (30) can be subsequently converted to compounds of Formula (Ie) following the same sequence of steps as the one described above for the conversions of compound (6) and compound (21) to compounds (Id) and compound (Ii), respectively.

Compounds of Formula (Ih) may be prepared starting from a boronic acid of Formula (31)

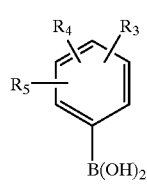

(31)

with a triazole of Formula (32), wherein X is Cr or Br;

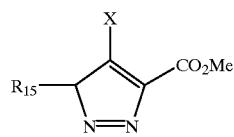

(32)

under standard Suzuki coupling conditions to provide an ester of Formula (33)

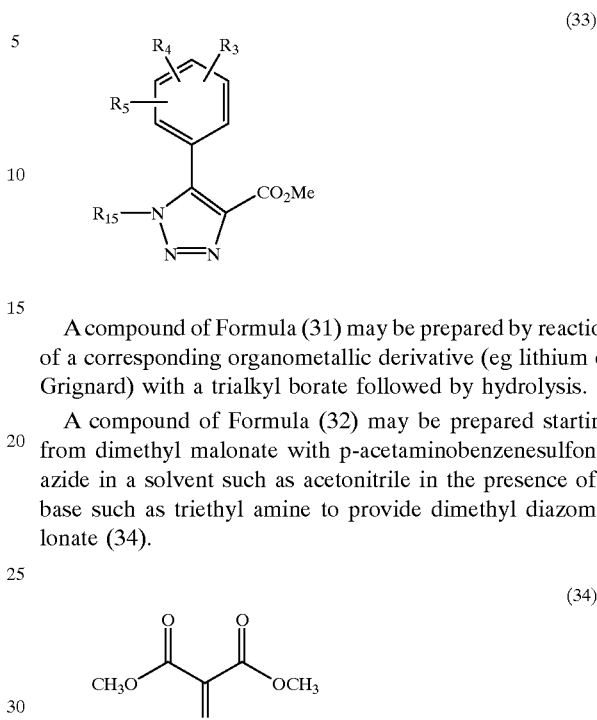

(33)

A compound of Formula (31) may be prepared by reaction of a corresponding organometallic derivative (eg lithium or Grignard) with a trialkyl borate followed by hydrolysis.

A compound of Formula (32) may be prepared starting from dimethyl malonate with p-acetaminobenzenesulfonyl azide in a solvent such as acetonitrile in the presence of a base such as triethyl amine to provide dimethyl diazomalonate (34).

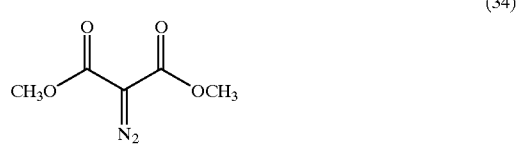

(34)

Treatment of diazomalonate of Formula (34) with an amine of Formula (35)

(35)

followed by acidic work up provides a triazole of Formula (36)

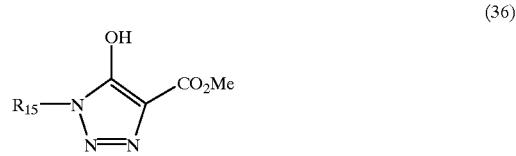

(36)

Reaction of a compound of Formula (36) with $PX_5$, whereas X is Br or Cl, in the presence of potassium carbonate in dimethylformamide affords a compound of Formula (32).

Compounds of Formula (Ij) may be prepared starting from an analine of Formula (37)

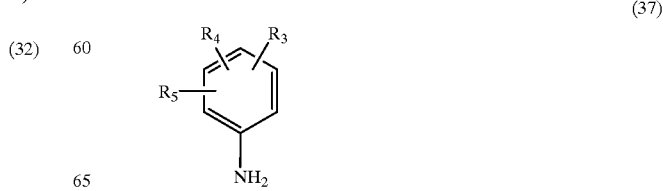

(37)

with a diketone of Formula of (38)

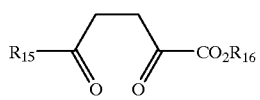

in a suitable solvent such as ethyl alcohol at reflux to provide a pyrrole of Formula (39).

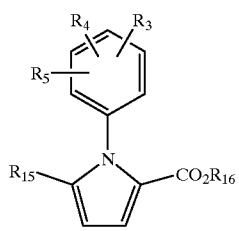

A diketone of Formula of (38) can be prepared by reacting of a,b-unsaturated ketone of Formula (40)

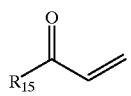

with a silyl enol ether of Formula (41)

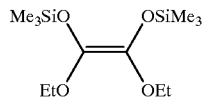

in the presence of Lewis acid such as zinc chloride in a suitable solvent such as dichloromethane followed by acidic hydrolysis. Compounds of Formula (33) and compounds of Formula (39) can be subsequently converted to compounds of Formula (Ih) and compounds of Formula (Ij), respectively, following the same sequence of steps as the one described above for the conversions of compound (6), compound (21) and compound (30) to compounds (Id), compound (Ii) and compound (Ie), respectively.

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavouring or colouring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regiment for parenteral administration is suitably about 0.001 mg/Kg to 40 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the invention are administered in accordance with the present invention.

The biological activity of the compounds of Formula (I) are demonstrated by the following tests:

I. Binding Assay

A) CHO cell membrane preparation.

CHO cells stably transfected with human $ET_A$ and $ET_B$ receptors were grown in 245 mm×245 mm tissue culture plates in Dulbecco's modified Eagle's medium supplemented with 10% fetal bovine serum. The confluent cells were washed with Dulbecco's phosphate-buffered saline containing a protease inhibitor cocktail (5 mM EDTA, 0.5 mM PMSF, 5 ug/ml of leupeptin and 0.1 U/ml of aprotinin)

and scraped in the same buffer. After centrifugation at 800× g, the cells were lysed by freezing in liquid nitrogen and thawing on ice followed by homogenization (30 times using a glass dounce homogenizer) in lysis buffer containing 20 mM Tris HCl, pH 7.5, and the protease inhibitor cocktail. After an initial centrifugation at 800× g for 10 min to remove unbroken cells and nuclei, the supernatants were centrifuged at 40,000× g for 15 min and the pellet was resuspended in 50 mM Tris HCl, pH 7.5, and 10 mM $MgCl_2$ and stored in small aliquots at −70° C. after freezing in liquid $N_2$. Protein was determined by using the BCA method and BSA as the standard.

(B) Binding studies.

[$^{125}$I]ET-1 binding to membranes prepared from CHO cells was performed following the procedure of Elshourbagy et al. (1993). Briefly, the assay was initiated in a 100 ul volume by adding 25 ul of [$^{125}$I]ET-1 (0.2–0.3 nM) in 0.05% BSA to membranes in the absence (total binding) or presence (nonspecific binding) of 100 nM unlabeled ET-1. The concentrations of membrane proteins were 0.5 and 0.05 ug per assay tube for $ET_A$ and $ET_B$ receptors, respectively. The incubations (30° C. 60 min) were stopped by dilution with cold buffer (20 mM Tris HCl, pH 7.6, and 10 mM $MgCl_2$) and filtering through Whatman GF/C filters (Clifton, N.J.) presoaked in 0.1% BSA. The filters were washed 3 times (5 ml each time) with the same buffer by using a Brandel cell harvester and were counted by using a gamma counter at 75% efficiency.

The following examples are illustrative and are not limiting of the compounds of this invention.

EXAMPLE 1

(E)-3-[1-n-Butyl-5-[2-(2-carboxy-6-chlorophenyl)methoxy-4-chlorophenyl]-1H-pyrazol-4-yl]-2-[(5-methoxy-2,3-dihydrobenzofuran-6-yl)methyl]-prop-2-enoic acid a) 2-Bromo-4-methoxyphenol To a solution of 4-methoxyphenol (13.00 g, 104.84 mmol) in DMF (50 mL) was added bromine (5.40 mL, 104.84 mmol) at 0° C. The reaction was allowed to warm to room temperature. After stirring for 2 h the reaction was quenched with water and extracted with ethyl acetate (3×200 mL). The combined organic extracts were washed with brine and dried ($Na_2SO_4$). Removal of the solvent under reduced pressure gave 21.28 g of the crude title compound as a dark oil: $^1$H NMR (250 MHz, $CDCl_3$) d 7.49 (b, 1 H), 6.96 (d, 1 H), 6.72-6.62 (m, 2 H), 3.71 (s, 3 H).

b) 2-Bromo-1-(2-chloroethoxy)-4-methoxybenzene

To a solution of 2-bromo-4-methoxyphenol (20.00 g, 98.04 mmol) in 1,2-dichloroethane (50.00 mL, 0.63 mol) was added sodium hydroxide (12.00 g, 0.29 mol) and benzyltriethylammonium chloride (3.00 g) in water (150 mL). The mixture was stirred at reflux for 24 h and extracted with ethyl acetate (3×150 mL). The combined organic extracts were washed with brine and dried ($Na_2SO_4$). After removing the solvent under reduced pressure, flash chromatography (1:1 diethyl ether/hexane) of the residue gave 14.20 g (66% over two steps) of the title compound as a yellow oil: $^1$H NMR (250 MHz, $CDCl_3$) d 7.09 (d, 1 H), 6.82-6.72 (m, 2 H), 4.27 (t, 2 H), 3.75 (t, 3 H), 3.71 (s, 3 H).

c) 5-Methoxy-2,3-dihydrobenzofuran

To a solution of 2-bromo-1-(2-chloroethoxy)-4-methoxybenzene (1.38 g, 5.22 mmol) in THF was added 190 mg (7.82 mmol) of Mg and MeI (3 mL). The mixture was sonicated for 2 h and stirred at room temperature for additional 20 h. The reaction was quenched with 3 N HCl (50 mL) and extracted with 1:1 hexane/ethyl acetate (3×50 mL). The combined organic extracts were washed with saturated $NaHCO_3$ brine and dried ($Na_2SO_4$). After removing the solvent under reduced pressure, flash chromatography (3:1 hexane/ethyl acetate) of the residue gave 0.66 g (85%) of the title compound as a colorless liquid: $^1$H NMR (400 MHz, $CDCl_3$) d 6.80 (d, 1 H), 6.70 (d, 1 H), 6.65 (dd, 1 H), 4.53 (t, 2 H), 3.75 (s, 3 H), 3.18 (t, 3 H).

d) 6-Bromo-5-methoxy-2,3-dihydrobenzofuran

To a solution of 5-methoxy-2,3-dihydrobenzofuran (1.00 g, 6.66 mmol) in dichloromethane (10 mL) was added hexamethylenetetraamine hydrobromide perbromide (2.79 g, 7.32 mmol) at −78° C. The reaction was allowed to warm to room temperature. After stirring for 3 h, the reaction was quenched with water and extracted with ethyl acetate (3×50 mL). The combined organic extracts were washed with brine and dried ($Na_2SO_4$). Removal of the solvent under reduced pressure gave 1.45 g (96%) of the title compound as a dark solid: $^1$H NMR (250 MHz, $CDCl_3$) d 7.00 (s, 1 H), 6.82 (s, 1 H), 4.57 (t, 2 H), 3.81 (s, 3 H), 3.15 (t, 2 H).

e) 5-Methoxy-2,3-dihydrobenzofuran-6-al

To a solution of 6-bromo-5-methoxy-2,3-dihydrobenzofuran (9.20 g, 40.35 mmol) in THF (50 mL) was dropwise added n-Butyl lithium (24.00 mL, 38.40 mmol) at −78° C. After stirring for 30 min. DMF (5.00 mL, 60.53 mmol) was added and the mixture was allowed to stir at room temperature for 2 h. The reaction was quenched with water and extracted with ethyl acetate (3×150 mL). The combined organic extracts were dried ($Na_2SO_4$) and the solvent was removed under reduced pressure. Flash chromatography (1:1 ether/hexane) of the residue afforded 5.42 g (76%) of the title compound as a yellow solid: $^1$H NMR (250 MHz, $CDCl_3$) d 10.32 (s, 1 H), 6.90 (s, 1 H), 6.82 (s, 1 H), 4.57 (t, 2 H), 3.91 (s, 3 H), 3.25 (t, 2 H).

f) Diethyl 2-(5-methoxy-2,3-dihydrobenzofuran-6-yliden)-malonate

To a solution of 5-Methoxy-2,3-dihydrobenzofuran-6-al (295 mg, 1.66 mmol) in benzene was added diethyl malonate (265 mg, 1.66 mmol), acetic acid (20 mL, 0.35 mmol) and piperidine (30 mL, 0.30 mmol). The mixture was heated at reflux for 3 h and then poured into 100 mL of water. This mixture was extracted with three 50 mL portion of ethyl acetate. The combined organic extracts were washed with brine and dried ($Na_2SO_4$). Removal of the solvent under reduced pressure gave quatitative yield of the title compound as a yellowish oil: $^1$H NMR (400 MHz, $CDCl_3$) d 8.02 (s, 1 H), 6.79 (s, 1 H), 6.78 (s, 1 H), 4.52 (t, 2 H), 4.30 (m, 4 H), 3.80 (s, 3 H), 3.18 (t, 2 H), 1.28 (m, 6 H).

g) Diethyl 2-(5methoxy-2,3-dihydrobenzofuranyl)methyl-malonate

To a solution of diethyl 2-(5-methoxy-2,3-dihydrobenzofuran-6-yliden)-malonate (1.80 g, 5.62 mmol) in ethanol (25 mL) was added sodium borohydride (0.22 g, 5.66 mmol) at room temperature. After stirring for 2 h the reaction was quenched with water and extracted with ethyl acetate (3×50 mL). The combined organic extracts were washed with brine and dried ($Na_2SO_4$). After removing the solvent under reduced pressure, flash chromatography (1:1 diethyl ether/hexane) of the dark residue afforded 1.47 (82%) of the title compound as a yellow oil: $^1$H NMR (250 MHz, $CDCl_3$) d 6.70 (s, 1 H), 6.54 (s, 1 H), 4.44 (t, 2 H, 4.12 (q, 2 H), 3.74 (m, 4 H), 3.11 (m, 4 H), 1.18 (t, 6 H).

h) Ethyl, hydrogen 2-(5-methoxy-2,3-dihydrobenzofuran-6-yl)methyl-malonate

To a solution of diethyl 2-(5-methoxy-2,3-dihydrobenzofuranyl)methyl-malonate (6.55 g, 20.34 mmol) in ethanol (50 mL) was added a solution of potassium hydroxide (1.35 g, 24.40 mmol) in water (10 mL). The reaction mixture was stirred at room temperature for 5 h. After concentrating the aqueous layer was washed with ether and acidified with concentrated HCl to pH 1 and extracted with ethyl acetate (3×100 mL). The organic extracts were washed with brine and dried ($Na_2SO_4$). Removal of the solvent under reduced pressure gave 5.26 g (88%) of the title compound as a white solid: $^1$H NMR (250 MHz, $CDCl_3$), d 11.43 (b, 1 H), 6.72 (s, 1 H), 6.58 (s, 1 H), 4.48 (t, 2 H), 4.16 (q, 2 H), 3.82 (t, 1 H), 3.75 (s, 3 H), 3.14 (t, 3 H), 1.20 (t, 3 H); MS (ESI) m/e 295.2 [M+H]$^+$: m.p.: 114–116° C.

i) 4-Chloro-2-hydroxyacetophenone

In a 500 mL of round bottom flask purged with argon was placed 26.00 g (0.153 mol) of 3-acetoxychlorobenzene, cooled with ice bath. Then 30.00 g (0.225 mol) of $AlCl_3$ was added in portions. The resulting mixture was heated to 140° C. for 2 h (caution: vigorous evolution of gas) and then cooled to 0° C., treated with 15 mL of conc. HCl in 100 mL of ice water, extracted with EtOAc (3×300 mL). The combined organic extracts were washed with brine and dried ($Na_2SO_4$). Removal of the solvent gave 24.00 g (92%) of the title compound as a light yellow liquid: $^1$H NMR (250 MHz, $CDCl_3$) d 1.07 (s, 1 H), 7.65 (d, J=8.6 Hz, 1 H), 6.98 (d, J=1.8 Hz, 1 H), 6.87 (dd, J=1.8, 8.6 Hz, 1 H), 2.61 (s, 3 H).

j) 4-Chloro-2-methoxymethoxyacetophenone

To a solution of 4-chloro-2-hydroxyacetophenone (22.00 g, 0.129 mol) in DMF (200 mL) was added $K_2CO_3$ (72.00 g, 0.516 mol) and bromomethylmethyl ether (0.134 mol). After stirring at 55° C. for 1 h, the mixture was poured into water and extracted with EtOAc (3×300 mL). The combined organic extracts were washed with brine and dried ($Na_2SO_4$) and removal of the solvent under reduced pressure gave 25.00 g (90%) of the title compound as an oil: $^1$H NMR (250 MHz, $CDCl_3$) d 7.68 (d, J=8.3 Hz, 1 H), 7.22 (d, J=1.8 Hz, 1 H), 7.00 (dd, J=1.8, 8.3 Hz, 1 H), 5.28 (s, 2 H), 3.53 (s, 3 H), 2.62 (s, 3 H).

k) Methyl 2-(4-chloro-2-methoxymethyl)benzoylacetate

To a solution of 4-Chloro-2-methoxymethoxyacetophenone (25.00 g, 0.116 mol) in dimethyl carbonate (150 mL) was added 7.5 g of 80% NaH (0.257 mol). After stirring for 10 min. at room temperature, the mixture was heated to 70° C. for 45 min. The resulting mixture was allowed to cool to room temperature and partitioned between water and ethyl acetate. The organic layer was separated and washed with brine and dried ($Na_2SO_4$). Removal of the solvent under reduced pressure gave 29.00 g (92%) of the title compound as an oil: MS (ESI) m/z 273 (M+H)$^+$; $^1$H NMR (400 MHz, $CDCl_3$) d 7.82 (d, J=8.4 Hz, 1 H), 7.25 (d, J=1.8 Hz, 1 H), 7.06 (dd, J=1.8, 8.4 Hz, 1 H), 5.25 (s, 2 H), 3.97 (s, 2 H), 3.72 (s, 3 H), 3.51 (s, 3 H).

l) Methyl (Z)-2-(4-chloro-2-methoxymethoxy)benzoyl-3-(dimethylamino)propenoate

A mixture of Methyl 2-(4-chloro-2-methoxymethoxy) benzoylacetate (24.00 g, 0.107 mol) and N,N-dimethylformamide dimethyl acetal (25.51 g, 0.214 mol) was heated to 90° C. overnight. Concentration under reduced pressure gave 34.86 g (100%) of the title compound as an oil: MS (ESI) m/z 328 (M+H)$^+$; $^1$H NMR (400 MHz, $CDCl_3$) d 7.71 (s, 1 H), 7.25 (d, 1 H), 7.13 (s, 1 H), 7.00 (d, 1 H), 5.12 (s, 2 H), 3.46 (s, 6 H), 3.44 (s, 6 H).

m) Methyl 1-n-butyl-5-(4-chloro-2-methoxymethoxyphenyl)-1H-pyrazol-4-yl carboxylate To a mixture of Methyl (Z)-2-(4-chloro-2-methoxymethoxy)benzoyl-3-(dimethylamino)propenoate (34.00 g, 0.104 mol) and n-butylhydrazine (37.00 g, 0.208 mol) in 600 mL of $MeOH/H_2O$ (9:1) was added NaOAc (84.86 g, 0.624 mol). The resulting mixture was stirred at room temperature overnight and then partitioned between water and $CH_2Cl_2$. The organic layer was separated and washed with brine and dried ($Na_2SO_4$). Removal of the solvent under reduced pressure gave 35.50 g (97%) of the title compound as an oil: MS (ESI) m/z 353 (M+H)$^+$; $^1$H NMR (400 MHz, $CDCl_3$) d 7.93 (s, 1 H), 7.04–7.22 (m, 3 H), 5.01 (dd, J=6.8, 9.5 Hz, 2 H), 3.75–3.92 (m, 2 H), 3.60 (s, 3 H), 3.30 (s, 3 H), 1.65 (m, 2 H), 1.12 (m, 2 H), 0.74 (t, 3 H).

n) 1-n-Butyl-5-(4-chloro-2-methoxymethoxyphenyl)-4-hydroxymethylpyrazole

To a solution of Methyl 1-n-butyl-5-(4-chloro-2-methoxymethoxyphenyl)-1H-pyrazol-4-yl carboxylate (10.00 g, 0.028 mol) in 200 mL of $CH_2Cl_2$ at 0° C. was added 85.2 mL of 1.5 M Dibal-H in toluene. After stirring for 1 h. the reaction was quenched with MeOH (100 mL) followed by addition of 35 mL of conc. HCl in 200 mL of water. The resulting mixture was stirred for 15 min. and extracted with $CH_2Cl_2$ (3×200 mL). The combined organic extracts were washed with brine and dried ($Na_2SO_4$). Removal of the solvent under reduced pressure gave 9.50 g (97%) of the title compound as a oil: MS (ESI) m/z 325 (M+H)$^+$; $^1$H NMR (400 MHz, $CDCl_3$) d 7.63 (s, 1 H), 7.13–7.29 (m, 3 H), 5.09 (s, 2 H), 4.36 (dd, 2 H), 3.80–3.98 (m, 2 H), 3.35 (s, 3 H), 1.70 (m, 2 H), 1.18 (m, 2 H), 0.81 (t, 3 H).

o) 1-n-Butyl-5-(4-chloro-2-methoxymethoxyphenyl)-1H-pyrazol-4-yl carboxaldehyde

To a solution of 1-n-Butyl-5-(4-chloro-2-methoxymethoxyphenyl)-4-hydroxymethylpyrazole (10.00 g, 30.86 mmol) in 150 mL of acetone at 0° C. was added of Jones' reagent until pink color persisted (30 mL), 60 mL of isopropyl alcohol was then added and the resulting mixture was stirred at room temperature for 15 min, diluted with 300 mL of cold water, extracted with $CH_2Cl_2$ (3×200 mL). The combined organic extracts were washed with brine and dried ($Na_2SO_4$). After removing the solvent under reduced pressure, flash chromatography of the residue with 25% EtOAc in hexane gave 5.50 g (56%) of the title compound as an oil: MS (ESI) m/z 323 (M+H)$^+$; $^1$H NMR (400 MHz, $CDCl_3$) d 9.54 (s, 1 H), 8.07 (s, 1 H), 7.35 (d, 1 H), 7.18 (m, 2 H), 5.13 (s, 2 H), 3.90–4.05 (m, 2 H), 3.38 (s, 3 H), 1.75 (m, 2 H), 1.20 (m, 2 H), 0.83 (t, 3 H).

p) Ethyl (E)-3-[1-n-butyl-5-(4-chloro-2-methoxymethoxyphenyl)-1H-pyrazol-4-yl]-2-[(5-methoxy-2,3-dihydrobenzofuran-6-yl)methyl]-2-propenoate To a mixture of 1-n-Butyl-5-(4-chloro-2-methoxymethoxyphenyl)-1H-pyrazol-4-yl carboxaldehyde (5.50 g, 17.08 mmol) and Ethyl, hydrogen 2-(5-methoxy-2,3-dihydrobenzofuran-6-yl)methyl-malonate (7.28 g, 24.70 mmol) in 50 mL in benzene was added piperidine (2.16 g, 25.41 mmol) and AcOH (0.51 g, 8.50 mmol), respectively. After heating at reflux for 3 h, the mixture was poured into water, extracted with EtOAc (3×100 mL). The combined organic extracts were washed with brine and dried ($Na_2SO_4$). After removing the solvent under reduced pressure, flash column chromatography of the residue with 25% EtOAc in hexane gave 4.50 g (48%) of the title compound as an oil: MS (ESI) m/z 555 (M+H)$^+$; $^1$H NMR (400 MHz, $CDCl_3$) d 7.53 (s, 1 H), 7.37 (s, 1 H), 7.32 (s, 1 H), 7.13 (m, 2 H), 6.78 (s, 1 H), 6.45 (s, 1 H), 5.11 (s, 2 H), 4.47 (t, 2 H), 4.14 (m, 2 H), 3.89 (m, 2 H), 3.85 (s, 3 H), 3.38 (s, 3 H), 3.16 (t, 2 H), 1.65 (m, 2 H), 1.20 (t, 3 H), 1.17 (m, 2 H), 0.79 (t, 3 H).

q) Ethyl (E)-3-[1-n-butyl-5-(4-chloro-2-hydroxyphenyl)-1H-pyrazol-4-yl]-2-[(5-methoxy-2,3-dihydrobenzofuran-6-yl)methyl]-2-propenoate To a solution of Ethyl (E)-3-[1-n-butyl-5-(4-chloro-2-methoxymethoxyphenyl)-1H-pyrazol-4-yl]-2-[(5-methoxy- 2,3-dihydrobenzofuran-6-yl)methyl]-2-propenoate (4.50 g, 8.10 mmol) in EtOH (60 mL) was added 0.6 mL of conc. HCl. After heating at reflux for 3 h, the mixture was concentrated and then diluted with EtOAc. The resulting mixture was washed with 5% $NaHCO_3$, brine and dried ($Na_2SO_4$). After removing the solvent, column chromatography of the residue with 25% EtOAc in hexane gave 2.65 g (64%) of the title compound as a solid: m.p. 158–160° C.; MS (ESI) m/z 511 (M+H)$^+$; $^1$H NMR (400 MHz, $CDCl_3$) d 7.58 (s, 1 H), 7.47 (s, 1 H), 7.02 (d, 1 H), 6.78 (s, 1 H), 6.62 (dd, 1 H), 6.59 (d, 1 H), 6.48 (s, 2 H), 5.50 (bs, 1 H), 4.48 (t, 2 H), 4.12 (m, 2 H), 3.85–3.95 (m, 4 H), 3.83 (s, 3 H), 3.81 (s, 3 H), 3.16 (t, 2 H), 1.67 (m, 2 H), 1.20 (t, 3 H), 1.17 (m, 2 H), 0.80 (t, 3 H).

r) Methyl 3-chloro-2-methylbenzoate

To a solution of 3-chloro-2-methylbenzoic acid (1.00 g, 5.86 mmol) in methanol (25 mL) was added 3 drops of sulfuric acid. The mixture was stirred at reflux for 18 h. After concentrating the residue was dissolved in ether, washed with 10% sodium hydroxide solution, brine and dried ($Na_2SO_4$). Removal of the solvent under reduced pressure gave 0.95 g (88%) of the title compound as a white solid: $^1$H NMR (250 MHz, $CDCl_3$) d 7.62 (d, 1 H), 7.41 (d, 1 H), 7.05 (t, 1 H), 3.82 (s, 3 H), 2.55 (s, 3 H).

s) 2-Chloro-6-methyl carboxylate benzylbromide

To a solution of methyl 3-chloro-2-methylbenzoate (1.30 g, 7.04 mmol) in benzene (20 mL) was added NBS (1.50 g, 8.45 mmol) and benzoyl peroxide (0.20 g, 0.83 mmol). After stirring at reflux for 18 h, the mixture was poured into water, and the resulting mixture was extracted with ethyl acetate (3×50 mL). The combined organic extracts were washed with brine and dried ($Na_2SO_4$). After removing the solvent under reduced pressure, flash column chromatography (1:1 ether/hexane) of the residue gave 1.87 g (82%) of the title compound as a dark oil: $^1$H NMR (250 MHz, $CDCl_3$) d 7.72 (d, 1 H), 7.55 (d, 1 H), 7.21 (t, 1 H), 5.09 (s, 2 H), 3.92 (s, 3 H).

t) Ethyl (E)-[1-n-butyl-5-[2-(2-methoxycarbonyl)phenylmethoxy-4-chloro-phenyl]-1H-pyrazol-4-yl]-2-[(5-methoxy-2,3-dihydrobenzofuran-6-yl)methyl]-2-propenoate To a solution of the ethyl (E)-[1-n-butyl-5-(2-hydroxy-4-chlorophenyl)-1H-pyrazol-4-yl]-2-[(5-methoxy-2,3-dihydrobenzofuran-6-yl)methyl]-2-propenoate (0.20 g, 0.39 mmol) and methyl 2-bromomethyl-3-chlorobenzoate (0.13 g, 0.47 mmol) in DMF (5 mL) was added sodium hydride (0.02 g, 0.59 mmol) at 0° C. The mixture was stirred at room temperature for 4 h. After an aqueous work up, extracting with ethyl acetate (3×15 mL), the combined organic extracts were washed with brine and dried ($Na_2SO_4$). After removing the solvent under reduced pressure, flash column chromatography (1:1 ethyl acetate/hexane) of the residue afforded the title compound as an oil (0.22 g, 80%). $^1$H NMR (250 MHz, $CDCl_3$) d 7.78 (d, 1 H), 7.55 (d, 1 H), 7.48 (s, 1 H), 7.32 (m, 2 H), 7.12 (d, 2 H), 6.75 (s, 1 H), 6.45 (s, 1 H), 5.55 (dd, J=10, 27.5 Hz, 2 H), 4.49 (t, 2 H), 4.10 (q, 2 H), 3.83 (s, 3 H), 3.77 (t, 2 H), 3.65 (s, 3 H), 3.15 (t, 2 H), 1.52 (quintet, 2 H), 1.20 (t, 3 H), 1.05 (sextet, 2 H), 0.75 (t, 3 H).

u) (E)-3-[1-n-Butyl-5-[2-(2-carboxy-6-chlorophenyl)methoxy-4-chlorophenyl]-1H-pyrazol-4-yl]-2-[(5-methoxy-2,3-dihydrobenzofuran-6-yl)methyl]-propen-2-oic acid To a solution of the ethyl (E)-[1-n-butyl-5-[2-[2-(methoxycarbonyl)-6-chlorophenylmethoxy]-4-chlorophenyl]-1H-pyrazol-4-yl]-2-[(5-methoxy-2,3-dihydrobenzofuran-6-yl)methyl]-2-propenoate (0.20 g, 0.29 mmol) in methanol (5 mL) was added a solution of sodium hydroxide (0.04 g, 0.87 mmol) in water (2 mL). The mixture was stirred at reflux for 18 h. The methanol was removed under reduced pressure and the aqueous layer was washed with ether. The aqueous layer was then acidified with concentrated HCl to pH 1 and extracted with ethyl acetate (3×50 mL). The combined organic extracts were washed with water, brine and dried ($Na_2SO_4$). Removal of the solvent gave a solid. Recrystallization from methanol yielded the title compound as a light yellow solid (0.17 g, 91%): $^1$H NMR (400 MHz $CDCl_3$) d 7.75 (d, 1 H), 7.80 (s, 1 H), 7.48 (m, 2 H), 7.33 (s, 1 H), 7.25 (t, 1 H), 7.10 (s, 1 H), 7.05 (m, 2 H), 6.65 (s, 1 H), 6.35 (s, 1 H), 5.49 (dd, J=10, 27.5 Hz, 2 H), 4.40 (t, 2 H), 3.79 (m, 5 H), 3.63 (t, 2 H), 3.05 (t, 2 H), 1.50 (quintet, 1 H), 1.30 (quintet. 1 H), 0.94 (quintet. 2 H), 0.60 (t, 3 H); MS(ESI) m/e 652.2 [M+H]$^+$; mp: 155–157° C. (methanol); Anal. ($C_{34}H_{32}Cl_2N_2O_7$) calcd: C, 62.62; H, 4.96; N, 4.30. found: C, 62.40; H, 5.32; N, 4.19.

EXAMPLE 2

(E)-3-[1-n-Butyl-5-[2-(2-carboxyphenyl)methoxy-4-chlorophenyl]-1H-pyrazol-4-yl]-2-[(5-methoxy-2,3-dihydrobenzofuran-6-yl)methyl]-prop-2-enoic acid a) Ethyl (E)-3-[1-n-Butyl-5-[2-(2-methoxycarbonyl)phenylmethoxy-4-chlorophenyl]-1H-pyrazol-4-yl]-2-[(5-methoxy-2,3-dihydrobenzofuran-6-yl)methyl]-2-propenoate Following the procedure of Example (1t) except substituting methyl 2-bromomethylbenzoate for methyl 2-bromomethyl-3-chlorobenzoate, the title compound was prepared in 85% yield.

b) Following the procedure of Example (1u) except substituting Ethyl (E)-3-[1-n-Butyl-5-[2-(2-methoxycarbonyl)phenylmethoxy-4-chlorophenyl]-1H-pyrazol-4-yl]-2-[(5-methoxy-2,3-dihydrobenzofuran-6-yl)methyl]-2-propenoate for ethyl (E)-[1-n-butyl-5-[2-[2-(methoxycarbonyl)-6-chlorophenylmethoxy]-4-chlorophenyl]-1H-pyrazol-4-yl]-2-[(5-methoxy-2,3-dihydrobenzofuran-6-yl)methyl]-2-propenoate, the title compound was prepared in 90% yield as a white solid: $R_f$ 0.58 (1:1 EtOAc/hexane with 1% AcOH); $^1$H NMR (400 MHz $CDCl_3$) d 8.19 (d, 1 H), 7.58 (s, 1 H), 7.53 (s, 1 H), 7.49 (t, 1 H), 7.30 (m, 2 H), 7.13 (m, 3 H), 6.77 (s, 1 H), 6.48 (s, 1 H), 5.52 (bs, 2 H), 4.45 (t, 2 H), 3.92 (m, 2 H), 3.82 (s, 3 H), 3.80 (bs, 2 H), 3.12 (t, 2 H), 1.65 (m, 2 H), 1.12 (m, 2 H), 0.76 (t, 3 H); MS(ESI) m/e 618 [M+H]$^+$; mp: 116–118° C. Anal. ($C_{34}H_{33}ClN_2O_7 \cdot 0.5H_2O$) calcd: C, 65.22; H, 5.47; N, 4.47. found: C, 65.03; H, 5.33; N, 4.37.

EXAMPLE 3

(E)-3-[1-n-Butyl-5-[2-(2-carboxyphenyl)methoxy-4-methoxyphenyl]-1H-pyrazol-4-yl]-2-[(dihydrobenzofuran-5-yl)methyl]-prop-2-enoic acid 98–99° C.

EXAMPLE 4

(E)-3-[1-n-Butyl-5-[2-(2-Carboxyphenyl)methoxy-4-methoxyphenyl]-1H-pyrazol-4-yl]-2-[(6-methoxy-2,3-dihydrobenzofuran-5-yl)methyl]-prop-2-enoic acid 104–106° C.

EXAMPLE 5

(E)-3-[1-n-Butyl-5-[2-(2-Carboxyphenyl)methoxy-4-methoxyphenyl]-1H-pyrazol-4-yl]-2-[(5-methoxy-2,3-dihydrobenzofuran-6-yl)methyl]-prop-2-enoic acid 198–200° C.

EXAMPLE 6

(E)-3-[1-n-Butyl-5-[2-(2-Carboxy-6-chlorophenyl)methoxy-4-methoxyphenyl]-1H-pyrazol-4-yl]-2-[(5-methoxy-2,3-dihydrobenzofuran-6-yl)methyl]-prop-2-enoic acid

EXAMPLE 7
(E)-3-[1-n-Butyl-5-[2-(2-Carboxy-5-chlorophenyl)methoxy-4-methoxyphenyl]-1H-pyrazol-4-yl]-2-[(5-methoxy-2,3-dihydrobenzofuran-6-yl)methyl]-prop-2-enoic acid 122–124° C.

EXAMPLE 8
(E)-3-[1-n-Butyl-5-[2-(2-Carboxy-4-chlorophenyl)methoxy-4-methoxyphenyl]-1H-pyrazol-4-yl]-2-[(5-methoxy-2,3-dihydrobenzofuran-6-yl)methyl]-prop-2-enoic acid 120–122° C.

EXAMPLE 9
(E)-3-[1-n-Butyl-5-[2-(3-carboxy-2-pyridyl)methoxy-4-methoxyphenyl]-1H-pyrazol-4-yl]-2-[(5-methoxy-2,3-dihydrobenzofuran-5-yl)methyl]-prop-2-enoic acid

EXAMPLE 10
(E)-3-[1-n-Butyl-5-[2-(cyclopentyloxy)-4-methoxyphenyl]-1H-pyrazol-4-yl]-2-[5-methoxy-2,3-dihydrobenzofuran-6-yl)methyl]-prop-2-enoic acid 156–158° C.

EXAMPLE 11
(E)-3-[1-n-Butyl-5-[2-(N,N-diethylamido)methoxy-4-methoxyphenyl)-1H-pyrazol-4-yl]-2-[(5-methoxy-2,3-dihydrobenzofuran-6-yl)methyl]-prop-2-enoic acid 178–180° C.

EXAMPLE 12
(E)-3-[1-n-Butyl-5-[2-(5-tetrazolyl)methoxy]-4-methoxyphenyl-1H-pyrazol-4-yl]-2-(5-methoxy-2,3-dihydrobenzofuran-6-yl)-methyl]-prop-2-enoic acid 128–130° C.

EXAMPLE 13
(E)-3-[1-n-Butyl-5-[2-(2-picolyl)oxy-4-methoxy]phenyl-1H-pyrazol-4-yl]-2-(5-methoxy-2,3-dihydrobenzofuran-6-yl)-methyl]-prop-2-enoic acid 132–135° C.

EXAMPLE 14
(E)-3-[1-n-Butyl-5-[2-(2-Carboxy-5-chlorophenyl)methoxy-4-chlorophenyl]-1H-pyrazol-4-yl]-2-[(5-methoxy-2,3-dihydrobenzofuran-6-yl)methyl]-prop-2-enoic acid 110–112° C.

EXAMPLE 15
(E)-3-[1-n-Butyl-5-[2-(4-methoxyphenoxy)-4-methoxyphenyl]-1H-pyrazol-4-yl]-2-[(5-methoxy-2,3-dihydrobenzofuran-6-yl)methyl]-prop-2-enoic acid 91–92° C.

EXAMPLE 16
(E)-3-[1-n-Butyl-5-[2-N-ethyl-5-tetrazolyl)methoxy]-4-methoxyphenyl-1H-pyrazol-4-yl]-2-[(5-methoxy-2,3-dihydrofuran-6-yl)methyl]-prop-2-enoic acid

EXAMPLE 17
(E)-3-[1-n-Butyl-5-[1-N-ethyl-5-tetrazolyl)methoxy]-4-methoxyphenyl-1H-pyrazol-4-yl]-2-[(5-methoxy-2,3-dihydrofuran-6-yl)methyl]-prop-2-enoic acid

EXAMPLE 18
Formulations for pharmaceutical use incorporating compounds of the present invention can be prepared in various forms and with numerous excipients. Examples of such formulations are given below.

Inhalant Formulation

A compound of Formula I, (1 mg to 100 mg) is aerosolized from a metered dose inhaler to deliver the desired amount of drug per use.

| Tablets/Ingredients | Per Tablet |
| --- | --- |
| 1. Active ingredient (Cpd of Form. I) | 40 mg |
| 2. Corn Starch | 20 mg |
| 3. Alginic acid | 20 mg |
| 4. Sodium Alginate | 20 mg |
| 5. Mg stearate | 1.3 mg |
| | 2.3 mg |

Procedure for tablets:

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its conversion to wet granules.

Step 3 The wet mass is converted to granules by passing it through an oscillating granulator using a No. 8 mesh (2.38 mm) screen.

Step 4 The wet granules are then dried in an oven at 140° F. (60° C.) until dry.

Step 5 The dry granules are lubricated with ingredient No. 5.

Step 6 The lubricated granules are compressed on a suitable table press.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then steriled by filtration through a 0.22 micron membrane filter and sealed in sterile containers.

We claim:

1. A compound of Formula (I):

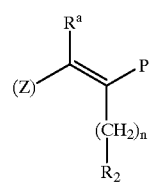

wherein (Z) is

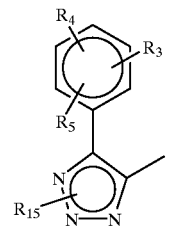

29

P is CO$_2$R$_6$ or C(O)N(R$_6$)S(O)$_q$R$_{10}$;

R$^a$ is independently hydrogen or C$_{1-6}$alkyl;

R$_1$ is independently hydrogen, Ar, C$_{1-6}$alkyl or C$_{1-6}$alkoxy;

R$_2$ is

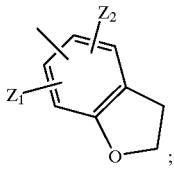

R$_3$ and R$_5$ are independently R$_{13}$OH, C$_{1-8}$alkoxy, S(O)$_q$R$_{11}$, N(R$_6$)$_2$, NO$_2$, Br, F, I, Cl, CF$_3$, NHCOR$_6$, R$_{13}$CO$_2$R$_7$, —X—R$_9$—Y, —X(C(R$_6$)$_2$)OR$_6$, —(CH$_2$)$_m$X'R$_8$ or —X(CH$_2$)$_n$R$_8$ where each methylene group within —X(CH$_2$)$_n$R$_8$ may be unsubstituted or substituted by one or two —(CH$_2$)$_n$Ar groups;

R$_4$ is independently R$_{11}$, OH, C$_{1-5}$alkoxy, S(O)$_q$R$_{11}$, N(R$_6$)$_2$, Br, F, I, Cl or NHCOR$_6$, wherein the C$_{1-5}$alkoxy may be unsubstituted or substituted by OH, methoxy or halogen;

R$_6$ is independently hydrogen or C$_{1-8}$alkyl;

R$_7$ is independently hydrogen, C$_{1-10}$alkyl, C$_{2-10}$alkenyl or C$_{2-8}$alkynyl, all of which may be unsubstituted or substituted by one or more OH, N(R$_6$)$_2$, CO$_2$R$_{12}$, halogen or XC$_{1-10}$alkyl; or R$_7$ is (CH$_2$)$_n$Ar;

R$_8$ is independently R$_{11}$, CO$_2$R$_7$, CO$_2$C(R$_{11}$)$_2$O(CO)XR$_7$, PO$_3$(R$_7$)$_2$, SO$_2$NR$_7$R$_{11}$, NR$_7$SO$_2$R$_{11}$, CONR$_7$SO$_2$R$_{11}$, SO$_3$R$_7$, SO$_2$R$_7$, P(O)(OR$_7$)R$_7$, CN, CO$_2$(CH$_2$)$_m$(C(O)N(R$_6$)$_2$, C(R$_{11}$)$_2$N(R$_7$)$_2$, C(O)N(R$_6$)$_2$, NR$_7$C(O)NR$_7$SO$_2$R$_{11}$, OR$_6$, or tetrazole which is substituted or unsubstituted by C$_{1-6}$alkyl;

R$_9$ is independently a bond, C$_{1-10}$alkylene, C$_{1-10}$alkenylene, C$_{1-10}$alkylidene, C$_{1-10}$alkynylene, all of which may be linear or branched, or phenylene, all of which may be unsubstituted or substituted by one of more OH, N(R$_6$)$_2$, COOH or halogen;

R$_{10}$ is independently C$_{1-10}$alkyl, N(R$_6$)$_2$ or Ar;

R$_{11}$ is independently hydrogen, Ar, C$_{1-8}$alkyl, C$_{2-8}$alkenyl, C$_{2-8}$alkynyl, all of which may be substituted or unsubstituted by one or more OH, CH$_2$OH, N(R$_6$)$_2$, or halogen;

R$_{12}$ is independently hydrogen, C$_{1-6}$alkyl, C$_{2-6}$alkenyl or C$_{2-7}$alkynyl;

R$_{13}$ is independently divalent Ar, C$_{1-10}$alkylene, C$_{1-10}$alkylidene, C$_{2-10}$alkenylene, all of which may be unsubstituted or substituted by one or more OH, CH$_2$OH, N(R$_6$)$_2$ or halogen;

R$_{14}$ is independently hydrogen, C$_{1-10}$alkyl, XC$_{1-10}$alkyl, Ar or XAr;

R$_{15}$ is independently hydrogen, Ar, C$_{1-6}$alkyl, or XAr;

R$_{16}$ is independently C$_{1-6}$alkyl or phenyl substituted by one or more C$_{1-6}$alkyl, OH, C$_{1-5}$alkoxy, S(O)$_q$R$_6$, N(R$_6$)$_2$, Br, F, I, Cl, CF$_3$ or NHCOR$_6$;

X is independently (CH$_2$)$_n$, O, NR$_6$ or S(O)$_q$;

X' is independently O, NR$_6$ or S(O)$_q$;

Y is independently CH$_3$ or X(CH$_2$)$_n$Ar;

30

Ar is:

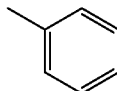

(a)

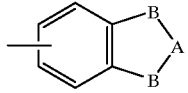

(b)

naphthyl, indolyl, pyridyl, thienyl, oxazolidinyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more Z$_1$ or Z$_2$ groups;

A is independently C=O, or (C(R$_6$)$_2$)$_m$;

B is independently —CH$_2$— or —O—;

Z$_1$ and Z$_2$ are independently hydrogen, XR$_6$, C$_{1-8}$alkyl, (CH$_2$)$_q$CO$_2$R$_6$, C(O)N(R$_6$)$_2$, CN, (CH$_2$)$_n$OH, NO$_2$, F, Cl, Br, I, N(R$_6$)$_2$, NHC(O)R$_6$, O(CH$_2$)$_m$C(O)NR$_a$SO$_2$R$_{16}$, (CH$_2$)$_m$OC(O)NR$_a$SO$_2$R$_{16}$, O(CH$_2$)$_m$NR$_a$C(O)NR$_a$SO$_2$R$_{16}$ tetrazolyl which may be substituted or unsubstituted by C$_{1-6}$alkyl, CF$_3$ or C(O)R$_6$;

m is independently 1 to 3;

n is independently 0 to 6;

q is independently 0, 1 or 2;

provided R$_3$, R$_4$ and R$_5$ are not O—O(CH$_2$)$_n$Ar or O—OR$_6$;

or a pharmaceutically acceptable salt thereof.

2. A compound of Formula (I) wherein P is CO$_2$R$_6$; R$_1$ is hydrogen; R$_3$ and R$_5$ are independently hydrogen, CO$_2$R$_6$, OH, C$_{1-8}$alkoxy, C$_{1-8}$alkyl, N(R$_6$)$_2$, NO$_2$, Br, F, Cl, I, R$_{13}$CO$_2$R$_7$, X(CH$_2$)$_n$R$_8$, (CH$_2$)mX'R$_8$, or X(C(R$_6$)$_2$)$_m$OR$_6$; R$_4$ is hydrogen, OH, C$_{1-5}$alkoxy, N(R$_6$)$_2$, Br, F, Cl, I, NHCOCH$_3$, or S(O)$_q$ C$_{1-5}$alkyl wherein the C$_{1-5}$alkyl may be unsubstituted or substituted by OH, methoxy or halogen; R$_6$ is hydrogen, methyl or ethyl; R$_7$ is hydrogen, C$_{1-10}$alkyl, C$_{2-10}$alkenyl or C$_{2-8}$alkynyl, all of which may be unsubstituted or substituted by one or more OH, N(R$_6$)$_2$, CO$_2$R$_{12}$, halogen, or R$_7$ is (CH$_2$)$_n$Ar wherein n is zero or 1 and Ar is substituted phenyl; R$_{11}$ is hydrogen, phenyl, pyridyl all of which may be substituted or unsubstituted by one or two C$_{1-4}$alkyl groups; C$_{1-8}$alkyl, C$_{2-8}$alkenyl, C$_{2-8}$alkynyl, all of which may be substituted or unsubstituted by one or more OH, CH$_2$OH, N(R$_6$)$_2$, or halogen; R$_{12}$ is hydrogen or C$_{1-6}$alkyl; R$_{13}$ is phenyl, pyridyl, or C$_{2-10}$alkylene, all of which may be unsubstituted or substituted by one or more CO$_2$R$_6$, OH, CH$_2$OH, N(R$_6$)$_2$, or halogen; R$_{15}$ is hydrogen or C$_{1-6}$alkyl; and (Z) is (d).

3. A compound of claim 2 wherein P is CO$_2$H; R$_1$ is hydrogen; Z$_1$ and Z$_2$ are independently hydrogen, CO$_2$R$_6$, (CH$_2$)$_n$OH, C$_{1-4}$alkyl or C$_{1-6}$alkoxy; R$_3$ is Br, Cl, C$_{1-8}$alkoxy or X(CH$_2$)$_n$R$_8$, wherein X is O, n is 0, 1 or 2, and R$_8$ is selected from: CO$_2$H, OH, tetrazolyl optionally substituted by C$_{1-8}$alkyl; CONR$_7$SO$_2$R$_{11}$ wherein R$_7$ is H or C$_{1-8}$alkyl, R$_{11}$ is C$_{1-8}$alkyl or phenyl optionally substituted by Br, Cl, F, C$_{1-8}$alkyl; or R$_8$ is phenyl or pyridyl substituted by one or more Br, Cl, CO$_2$H, CH$_2$OH; R$_5$ is methoxy or N(R$_6$)$_2$ wherein R$_6$ is H or methyl; R$_4$ is hydrogen; R$_6$ is hydrogen, methyl or ethyl; R$_7$ is hydrogen, C$_{1-10}$alkyl, C$_{2-10}$alkenyl or C$_{2-8}$alkynyl, all of which may be unsubstituted or substituted by one or more OH, $N(R_6)_2$, $CO_2R_{12}$, halogen, or $R_7$ is $(CH_2)_nAr$ wherein $R_7$ is $(CH_2)_nAr$ and n is preferably zero or 1 and Ar is preferably phenyl substituted or unsubstituted by halogen or $C_{1-5}$ alkoxy; $R_{11}$ is hydrogen, phenyl, pyridyl all of which may be substituted of unsubstituted by one or two $C_{1-4}$alkyl groups; $C_{1-8}$alkyl, $C_{2-8}$alkenyl, $C_{2-8}$alkenyl, all of which may be substituted or unsubstituted by one or more OH, $CH_2OH$, $N(R_6)_2$, or halogen; $R_{12}$ is hydrogen or $C_{1-6}$alkyl; $R_{13}$ is phenyl, pyridyl, or $C_{2-10}$alkylene, all of which may be unsubstituted or substituted by one or more $CO_2R_6$, OH, $CH_2OH$, $N(R_6)_2$, or halogen, $R_{15}$ is hydrogen, ethyl, isopropyl, n-butyl, cyclopropylmethyl or cyclopropylethyl; and (Z) is (d).

4. A pharmaceutical composition comprising a compound of claim 1 and a pharmaceutically acceptable carrier.

5. A method of treatment of diseases caused by an excess of endothelin comprising administering to a subject in need thereof, an effective amount of an endothelin receptor antagonist of claim 1.

6. A method of treating hypertension, renal failure or cerebrovascular disease which comprises administering to a subject in need thereof, an effective amount of a compound of claim 1.

7. A method for the treatment of chronic renal failure which comprises administering to a subject in need thereof, an effective amount of a compound of claim 1.

8. A method of treatment of benign prostatic hypertrophy which comprises administering to a subject in need thereof, an effective amount of a compound of claim 1.

9. A method of treatment of congestive heart failure which comprises administering to a subject in need thereof, an effective amount of a compound of claim 1.

10. A method of treatment of unstable angina, coronary vasospasm and myocardial salvage, which comprises administering to a subject in need thereof, an effective amount of a compound of claim 1.

11. A method of preventing or treating restenosis which comprises administering to a subject in need thereof, an effective amount of a compound of claim 1.

12. A method of treatment of pulmonary hypertension which comprises administering to a subject in need thereof, an effective amount of a compound of claim 1.

13. A method of treatment of atherosclerosis which comprises administering to a subject in need thereof, an effective amount of a compound of claim 1.

14. A method of preventing and treating the sequelae of diabetes which comprises administering to a subject in need thereof, an effective amount of a compound of claim 1.

15. A method of treatment of stroke or subarachnoid hemorrhage which comprises administering to a subject in need thereof, an effective amount of a compound of claim 1.

* * * * *